US006432883B1

(12) United States Patent
Kinnersley (10) Patent No.: US 6,432,883 B1
(45) Date of Patent: Aug. 13, 2002

(54) METHODS OF TREATING PLANTS WITH GLYCOLIC ACID

(75) Inventor: Alan M. Kinnersley, East Lansing, MI (US)

(73) Assignee: Emerald BioAgriculture Corporation, Lansing, MI (US)

( * ) Notice: Subject to any disclaimer, the term of this patent is extended or adjusted under 35 U.S.C. 154(b) by 0 days.

(21) Appl. No.: 09/552,917

(22) Filed: Apr. 20, 2000

(51) Int. Cl.[7] .............................................. A01N 37/02
(52) U.S. Cl. ...................... 504/320; 514/557; 435/244
(58) Field of Search ..................... 504/320; 435/244; 514/557

(56) References Cited

U.S. PATENT DOCUMENTS

| | | | |
|---|---|---|---|
| 3,679,392 A | | 7/1972 | Strauss et al. ................. 71/89 |
| 3,957,578 A | * | 5/1976 | Narita et al. ................... 195/11 |
| 4,246,343 A | * | 1/1981 | Wilkins et al. ................ 435/32 |
| 4,813,997 A | | 3/1989 | Kinnersley et al. ............. 71/66 |
| RE35,320 E | | 8/1996 | Kinnersley et al. ......... 504/161 |
| 5,593,947 A | | 1/1997 | Kinnersley et al. ......... 504/283 |
| 5,814,582 A | | 9/1998 | Koskan et al. .............. 504/320 |
| 6,008,256 A | | 12/1999 | Haraguchi et al. .......... 514/626 |

FOREIGN PATENT DOCUMENTS

| | | | |
|---|---|---|---|
| EP | 208 403 A1 | 1/1987 | .................... 37/50 |
| WO | WO 98/00012 | 1/1998 | |

OTHER PUBLICATIONS

Zelitch, I., Biochemical control of stomatal opening and the synthesis of glycolic acid in leaves, Fed. Proc. 24:868–872 (1965).

Zelitch, I., The Relationship of Glycolic Acid to Respiration and Photosynthesis in Tobacco Leaves, J. Biol. Chem. 234(12):3077–3081 (1959).

Tillberg, E., Glycolate and glyoxylate stimulation of growth in Lemna gibba, Physiol. Plant. 50:158–160 (1980).

* cited by examiner

*Primary Examiner*—S. Mark Clardy
(74) *Attorney, Agent, or Firm*—Woodard, Emhardt, Naughton, Moriarty & McNett (57) ABSTRACT

Methods for increasing the resistance of a plant to the effects of plant stress utilizing glycolic acid, a salt thereof, or a mixture thereof, are described. Methods for stimulating plant growth utilizing an ammonium salt of glycolic acid are also described. Further described are methods for stimulating microbial growth utilizing selected amounts of glycolic acid, a salt thereof, or a mixture thereof.

27 Claims, 5 Drawing Sheets

METHODS OF TREATING PLANTS WITH GLYCOLIC ACID

BACKGROUND OF THE INVENTION

The present invention relates generally to methods for treating plants that increase the resistance or tolerance of a plant to the effects of plant stress and/or stimulate plant growth.

Biological stress has been defined as "any change in environmental conditions that might reduce or adversely change a plant's growth or development" (J. Levitt, 1972, *Responses of Plants to Environment Stresses*, Academic Press, Inc., New York and London). Adverse environmental conditions such as water deprivation, pathogen attack, salinity and unfavorable growing temperatures are common stresses that limit agriculture yields. For example, it has been estimated that the world rice production would decrease 50% if the world mean temperature dropped by only 1.0° C. (F. B. Salisbury & C. W. Ross, *Stress Physiology in Plant Physiology*, 1985, published by Wadsworth Inc.). Moreover, a comparison of average and record yields of eight major crops showed that average yields were only one-third to one-seventh of record yields (Boyer, *Science*, 1982, 218:443–448). More than 70% of the loss of potential yields was attributed to unfavorable growing conditions caused by factors such as weeds, disease, soil, climate, etc. (Id.).

Unlike animals, which are able to move into less stressful environments, plants rely on chemical defenses to respond to stress. When plants are exposed to unfavorable high growing temperatures, normal protein synthesis is reduced and rapid synthesis of heat shock proteins commences (J. L. Key and Y. M. Chem 1981, *Proc. Natl. Acad. Science* 78:3526–3530). Similarly, low temperature acclimation in plants is associated with the synthesis of specific, extremely hydrophilic proteins which act as cryoprotectants, much like anti-freeze (J. G. Boothe et al., 1997, *Plant Physiol.* 113:367–376). In response to invasion of plant tissues by pathogens such as insects or fungi, stress-induced lignin deposition occurs to seal off the site of wounding (R. A. Dixon and N. L. Pawa, 1995, *Plant Cell* 7:1085–1097). Many plants respond to drought and salinity stress by accumulating high levels of protein, which is believed to protect plant tissues from osmotic stress (G. R. Stervant, et al., 1976, *Plant* 120, 279–289).

Even though plants have developed specific patterns of stress-mediated metabolism in response to various environmental and biological challenges, adverse environmental conditions still limit agriculture yields. Efforts to mitigate or increase the resistance of a plant to the effects of plant stress have included complex methodologies that are both time-consuming and expensive. For example, in order to inhibit pathogenic conditions of plants, recombinant DNA technology has been used to incorporate genes into the plant genome that encode polypeptide and complementary oligonucleotide inhibitors. Such a method, directed at mitigating the effects of pathogen stress, would not be expected to mitigate, or increase the resistance of a plant to, the effects of different forms of stress. For example, such a method would not be expected to protect plants from heat or cold stress. Therefore, it is usually necessary to incorporate other genes into the plant's genome that will be effective in eliminating the particular stress involved. A simple, safe and cost-effective method to increase the resistance of a plant to the effects of a wide variety of plant stresses is needed. The present invention addresses this need.

SUMMARY OF THE INVENTION

It has been discovered that application of glycolic acid to plants increases the resistance of the plants to the effects of plant stress. Accordingly, the present invention provides methods for increasing the resistance of plants to the effects of plant stress utilizing glycolic acid.

In one aspect of the invention, a method of increasing the resistance of a plant to the effects of plant stress includes treating the plant with glycolic acid, a salt thereof, or a mixture thereof. The plant is typically treated with an amount of glycolic acid effective in increasing the resistance of the plant to the effects of plant stress. The method preferably includes treating the plant with the aforementioned compounds or compositions prior to the occurrence of plant stress. In one embodiment, the salt of glycolic acid is an ammonium salt.

In yet another aspect of the present invention, a method of increasing the resistance of a plant to the effects of plant stress includes predicting when a stressful condition will arrive and then treating the plant with glycolic acid, a salt thereof, or a mixture thereof, prior to the occurrence of plant stress.

It has also unexpectedly and surprisingly been discovered that application of an ammonium salt of glycolic acid stimulates plant growth significantly more than glycolic acid. Accordingly, in yet another aspect of the invention, methods of treating plants are provided that include treating the plant with an effective amount of an ammonium salt of glycolic acid.

It is an object of the present invention to provide methods of increasing the resistance of a plant to the effects of plant stress.

It is a further object of the invention to provide methods for treating plants to stimulate plant growth.

These and other objects and advantages of the present invention will be apparent from the following description.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods of treating plants with glycolic acid, including methods for increasing the resistance of plants to the effects of diverse environmental and biological stresses, as well as methods for stimulating plant growth. It has been discovered that application of glycolic acid, or a salt thereof, or a mixture thereof, to plants increases the resistance of the plants to the effects of plant stress. Such increased resistance includes the ability of the plants to tolerate the effects of plant stress. It has also unexpectedly been discovered that application of an ammonium salt of glycolic acid stimulates plant growth more than an equivalent amount of glycolic acid alone. Yet another unexpected discovery is that glycolic acid has microbial growth-promoting effects, and that the ammonium salt of glycolic acid stimulates microbial growth more than equivalent amounts of glycolic acid alone. In one aspect of the invention, a method includes treating a plant with glycolic acid, a salt thereof, or a mixture thereof, in an amount effective to increase the resistance of the plant to the effects of plant stress. The method may further include predicting when a stressful condition will arrive prior to treating the plant. The methods of the invention may be useful in increasing the resistance of a plant to the effects of plant stress in order to prevent the effects of plant stress from occurring. In another aspect of the invention, a method includes treating the plant with an ammonium salt of glycolic acid, typically in an amount effective to stimulate plant growth. A further aspect of the invention provides methods of stimulating microbial growth by treating the microbes with an effective amount of glycolic acid, a salt thereof, or a mixture thereof.

In a first aspect of the invention, methods of increasing the resistance of a plant to the effects of plant stress are provided. In one embodiment of the invention, a method includes treating the plant with glycolic acid, a salt thereof, or a mixture thereof. The plant is typically treated with an amount of glycolic acid, a salt thereof, or a mixture thereof, effective to increase the resistance of the plant to the effects of plant stress. The composition may be applied alone or with a carrier medium as described below.

Glycolic acid may be obtained from commercial sources, natural sources, or may be synthesized by methods known to the art. Any form of glycolic acid may be used, including various salts thereof known to the art. Illustrative carboxylate salts include salts formed from alkali metals, such as sodium and potassium, although others will also be useful. One preferred form of glycolic acid is 99% high purity crystalline glycolic acid (Glypure®) available from DuPont (Wilmington, Del.). A more preferred form of glycolic acid is an ammonia-neutralized form of Glypure® as herein described.

The amount of glycolic acid effective in increasing the resistance of a plant to the effects of plant stress will depend on various factors, including the type of plant, the quantity of plants treated, and the nature and degree of stress and can be readily determined by the skilled artisan. For example, the plant may be treated with a specified amount of glycolic acid and its effect on the resistance of the plant to the effects of plant stress may be determined by observing, compared to untreated plants, increases in dry weight of the plant, increases in the number of germinated seeds, or by making other relevant observations. In the case of stress due to infection by pathogens, one may observe, for example, discoloration, lesion depth, stem decomposition or may make other observations as described in the examples. Preferred concentrations of glycolic acid include from about 1 ppm to about 10,000 ppm [about 0.013 oz/acre (oz/A) to about 8.3 lbs/A] [about 0.93 g/hectare (g/ha) to about 9.4 kg/ha], although lower concentrations are more preferred. For example, more preferred concentrations include about 1 ppm to about 5,000 ppm [about 0.013 oz/A to about 4.2 lbs/A] [about 0.93 g/ha to about 4.7 kg/ha], about 1 ppm to about 1000 ppm [about 0.013 oz/A to about 0.83 lbs/A] [about 0.93 g/ha to about 0.94 kg/ha] and about 2 ppm to about 500 ppm [about 0.027 oz/A to about 0.42 lbs/A] [about 1.9 g/ha to about 0.47 kg/ha]. It is also noted that ranges as stated above, except having a lower value of about 0.5 ppm, are also envisioned. All amounts in ppm are on a weight/volume basis. Moreover, the application rates in brackets above are derived for a treatment utilizing a standard volume of 100 gallons of the specified solutions dispersed over 1 acre.

In yet another aspect of the invention, a method of increasing the resistance of a plant to the effects of plant stress is provided that includes initially predicting when a stressful condition will arrive and then treating the plant with the compound or compositions described above in the amounts described above prior to the occurrence of plant stress. For example, if severe frost is predicted, the plant may be treated with the compound or compositions described herein prior to the cold temperature stress. As another example, if disease is more likely to occur during certain times of the year, the plants may be treated prior to these times.

In a further aspect of the invention, a plant may be treated with a composition that includes glycolic acid, a salt thereof, or a mixture thereof, and an additional active agent. "Active agent", as used herein, refers to an agent, such as an agricultural agent, that has a beneficial effect on the plant with respect to nutrition, and the resistance against, or reduction of, the effects of plant stress. Accordingly, the active agent may include a wide variety of fertilizers, pesticides and herbicides known in the art. Suitable fertilizers are disclosed, for example, in Kirk-Othmer, *Concise Encyclopedia of Chemical Technology*, 4th Ed. v. 10, pp. 433–514(1993). Other greening agents fall within the definition of "active agent" as well, including minerals such as magnesium and iron. The pesticides protect the plant from pests or disease and may be either chemical or biological and include fungicides, bactericides, insecticides and anti-viral agents as known in the art. As glycolic acid and its salts increase pesticidal control, lower quantities of the pesticide may be needed when the pesticide is combined with glycolic acid, a salt thereof or a mixture thereof.

The amount of the additional active agent included in the composition may vary depending on the nature of the active agent and may be determined by the skilled artisan. One may also follow the directions from the manufacturer of the active agent in determining the amount of additional active agent to use.

In yet another aspect of the invention, a method of treating a plant is provided that includes treating the plant with an ammonium salt of glycolic acid. The composition preferably includes an amount of ammonium glycolate effective in stimulating plant growth. This amount depends on several factors, including the type of plant and the quantity of plants treated. However, due to its superior plant growth-stimulating ability, smaller amounts of ammonium glycolate may be used compared to glycolic acid to obtain a similar plant growth-stimulating effect. Therefore, although the plants may be treated with the amounts described above, it is preferred to treat plants with about 1 ppm to about 5000 ppm [about 0.013 oz/A to about 4.2 lbs/A] [about 0.93 g/ha to about 4.7 kg/ha] and more preferably with about 1 ppm to about 300 ppm [about 0.013 oz/A to about 0.25 lbs/A] [about 0.93 g/ha to about 0.28 kg/ha] of the ammonium salt of glycolic acid to stimulate plant growth. The plant may be treated with the ammonium salt of glycolic acid alone or, in other embodiments, an additional active agent may be co-administered with the salt as described above for glycolic acid. Moreover, as also described above, the plant may also be treated with a composition that includes ammonium glycolate and glycolic acid.

The compounds and compositions described above are preferably combined with a carrier medium as known in the art. The compounds and compositions may, for example, be combined with water, such as tap water or with distilled water to which has been added selected minerals. Alternatively, the compositions of the present invention may be applied as a solid. In such a form, the solid is preferably applied to the soil.

The compositions may further include agricultural additives or formulation aids known to those skilled in the art. Such additives or aids may be used to ensure that the compositions disperse well in a spray tank, stick to or penetrate plant surfaces (particularly leaf or other foliage surfaces) as well as provide other benefits to the plant. For example, surfactants, dispersants, humectants, and binders may be used to disperse the compounds or compositions described herein in a spray tank as well as to allow the compounds or compositions to adhere to and/or penetrate the plant surfaces.

The compounds and compositions of the present invention are typically applied to the foliage of the plant but may also be administered as a soil drench. Furthermore, when plants are grown hydroponically, the compounds and compositions may be applied to the aqueous solution in which the plants are grown. The compositions are further preferably applied by spraying. Moreover, the compounds and compositions may also be applied as a seed treatment.

The compounds and compositions may be used to increase the resistance of a plant to a wide variety of plant stresses, including, for example, mechanical damage stress, nutrient stress, heat stress, cold stress, drought stress, water stress, salt stress and pathogen stress (including insect, bacterial, fungal and viral pathogen stresses).

The compounds or compositions described herein are preferably applied pre-harvest in the methods of increasing the resistance of the plants to the effects of plant stress. The compounds or compositions may also be applied post-harvest in such methods, especially to prevent pathogen stress. Moreover, the compounds or compositions are preferably applied prior to the occurrence of stress.

The methods described above may be applied to treat a wide variety of plants, including decorative or recreational plants or crops, but are particularly useful for treating commercial crops. Examples of plants and crops that may be treated in the present invention include monocotyledons, such as duckweed, corn, turf (including rye grass, Bermuda grass, Blue grass, Fescue), dicotyledons, including lettuce, cereals such as wheat, crucifers (such as rapeseed, radishes and cabbage), solanaceae (including green peppers, potatoes and tomatoes), and legumes such as soybeans and bush beans.

In yet another aspect of the invention, methods of treating microbes with glycolic acid, a salt thereof, or a mixture thereof are provided. It has surprisingly been discovered that treating microbes with selected concentrations of such compounds or compositions increases the growth of the microbes. In one form of the invention, a method includes treating a microbe with glycolic acid, a salt thereof, or a mixture thereof. In preferred forms of the invention, the microbe is treated with ammonium glycolate. The microbes may be treated while cultured in a liquid medium, or the growth-stimulating compounds/compositions may be added to a solid nutrient medium upon which the microbes are grown.

The microbes are generally treated with an amount of glycolic acid, a salt thereof, or a mixture thereof that is effective in stimulating microbial growth. It must be realized that if microbes are treated with too large of an amount of the compounds/compositions described herein, microbial death will occur. Although the microbes may be treated with larger amounts depending on the situation, the microbes are generally treated with no more than about 2,000 ppm (weight/volume) of the glycolic acid-containing compositions, although they are preferably treated with about 1 ppm to about 1000 ppm, and further about 1 ppm to about 500 ppm. The microbes may also be treated with similar amounts of ammonium glycolate. However, as ammonium glycolate is more effective than glycolic acid in stimulating microbial growth, less ammonium glycolate compared to glycolic acid may generally be used. A wide variety of microbes may be treated, including bacteria and fungi.

Reference will now be made to specific examples illustrating the compositions and methods described above. It is to be understood that the examples are provided to illustrate preferred embodiments and that no limitation to the scope of the invention is intended thereby. Unless otherwise noted, the glycolic acid used in the examples that follow was Glypure®, a 99% high purity crystalline glycolic acid from DuPont (Wilmington, Del.). Moreover, Duncan multiple comparison analyses for observed means at a confidence interval of 95% (i.e., $p \geq 0.95$) were performed to show mean separation and groupings for the data shown in FIGS. 1–5. In FIGS. 1–5, significant differences between any two groups being compared are present when no letters are shared between the two groups. General Linear Models (GLM) multivariate analyses at a significance level, or a level, of 0.05 were performed to determine the statistical significance relating to the data discussed in Examples 1–6. This includes an analysis of variance and is equivalent to a confidence interval of 95%, or a p value $\geq 0.95$.

EXAMPLE 1

Effect of Glycolic Acid on the Resistance and/or Tolerance of Lettuce to the Effects of Pathogen Stress Waldmann's MTO dark green Grand Rapids leaf lettuce seed, lot#15529, was purchased from Johnny's Selected Seeds, Albion, Me., and grown 8 plants per 1 gallon pot, 1 pot per experimental unit and 3 experimental units per each of 4 replications. The plants were spray-treated first following "row closure" and again 14 days later with 8 ml per pot. The pathogen stress (*Sclerotinia minor* hyphal fragments and sclerotia, cultured on potato dextrose agar) was applied to the plant stems at the soil/stem interface at 14 days following the second treatment application.

Treatments consisted of non-inoculated and inoculated groups of non-treated (NTC), water and 0.05% surfactant-blank (SB) controls and 15 and 60 ppm of glycolic acid.

Disease assessment was made just prior to harvest by means of a 1–9 based rating scale. Extensive decomposition of the controls made accurate yield fresh and dry weights impossible. The results in Table 1 below show the data for each treatment and the rating scale definitions.

TABLE 1

| Treatment | Disease Severity Rating | Rating Scale Definitions |
|---|---|---|
| NTC | 7.2 | 1) stem non-symptomatic |
| Water | 6.3 | 2) lesion beyond epidermis |
| SB | 7.4 | 3) stem decomposition |
| 15 ppm | 3.0* | & vascular discoloration |
| 60 ppm | 3.5* | 4) External hyphae, stem intact |
| | | 5) External mat, stem rot through |
| | | 6) white sclerotia forming |
| | | 7) black sclerotia in mycelium |
| | | 8) rot 2–3" up stem |
| | | 9) Sclerotia & vasc. tissue only remain |

*indicates a statistically significant improvement over all control treatments.

These data show a statistically significant ($\alpha=0.05$) decrease in the disease severity among all glycolic acid treated lettuce versus the control (i.e., NTC) lettuce.

EXAMPLE 2

Effect of Glycolic Acid on the Resistance and/or Tolerance of Cabbage to the Effects of Pathogen Stress Market Prize, F1 cabbage seed, lot 88955, was purchased from Harris Seeds, Inc., Rochester, N.Y. These were grown 8 plants per 1 gallon pot, 1 pot per experimental unit and 3 experimental units per each of 3 replications. The plants were spray-treated first at 4 true leaves and again 14 days later with 8 ml per pot. The pathogen stress (*Sclerotinia minor* hyphal fragments and sclerotia, cultured on potato dextrose agar) was applied to the plant stems at the soil/stem interface at 4 days following the second treatment application.

Treatments consisted of non-inoculated and inoculated groups of non-treated (NTC), water and 0.05% surfactant-blank (SB) controls and 1, 5, 10, 25, 37.5 and 75 ppm of glycolic acid.

Disease assessment was made just prior to harvest by means of a 1–9 based rating scale. Each plant was harvested at the soil line for yield fresh and dry weights. The results in Table 2 below show the data for each treatment and the rating scale definitions.

TABLE 2

| Treatment | Disease Severity Rating | Fresh Weight (g) | Dry Weight (g) |
|---|---|---|---|
| NTC | 3.3 | 320 g | 37.8 g |
| Water | 3.6 | 323 g | 38.1 g |
| SB | 2.8 | 329 g | 36.4 g |
| 1 ppm | 3.6 | 359 g | 38.3 g |
| 5 ppm | 3.7 | 346 g | 39.8 g |
| 10 ppm | 2.8 | 342 g | 40.9 g |
| 25 ppm | 2.2 | 364 g | 39.1 g |
| 37.5 ppm | 1.7* | 381* g | 39.0 g |
| 75 ppm | 2.0* | 354 g | 41.5* g |

*indicates a statistically significant improvement over all control treatments.

| Rating Scale |
|---|
| 1) hypocotyl non-symptomatic |
| 2) lesion into cortex |
| 3) cortex rot, vascular discolor |
| 4) External hyphae visible |
| 5) Mycelial mat at base, cortex digested through |
| 6) white sclerotia forming |
| 7) Sclerotia gray to black |
| 8) cortex rot above hypocotyl |
| 9) Sclerotia & vascular tissue remaining |

These data show a statistically significant ($\alpha=0.05$) decrease in the disease severity among the 37.5 and 75 ppm glycolic acid treated lettuce versus the control lettuce. The reduction in disease was associated with a statistically significant increase in fresh and dry weights with the 37.5 ppm and 75 ppm glycolate treatments, respectively.

EXAMPLE 3

Effect of Glycolic Acid on the Resistance and/or Tolerance of Wheat to the Effects of Pathogen Stress Kulm wheat seed, lot CR, was purchased from Albert Lea Seed House, Albert Lea, Minn. and grown 100 plants per 1 gallon pot, 3 pots per experimental unit and 1 experimental unit per each of 6 replications. The plants were spray-treated first at late-tillering to jointing and again at "in boot" to anthesis with 8 ml solution per pot. Aerial application of the pathogen stress (*Erysiphe graminis/Ooidium conidia* cultured on other Kulm wheat plants infected by incoming natural inoculum) was made to the plants at 14 days following the first treatment application, in addition to other naturally occurring inoculum.

Treatments consisted of non-inoculated and inoculated groups of non-treated (NTC), water and 0.05% surfactant-blank (SB) controls and 5, 25, and 50 ppm of glycolic acid.

Disease assessment was made 3 days prior to head harvesting using a 1–7 based severity scale and % incidence. A disease index [(1–7 based severity rating)(% incidence)/100] was created to better describe the compound effect. The results in Table 3 below show the data for each treatment and the rating scale definitions.

TABLE 3

| Treatment | Disease Index Leaves | Disease Index Heads |
|---|---|---|
| NTC | 25.0 | 45.0 |
| Water | 47.8 | 45.7 |
| SB | 43.2 | 37.0 |
| 5 ppm | 7.6* | 2.5* |
| 25 ppm | 7.0* | 13.4* |
| 50 ppm | 36.9 | 18.6* |

*indicates a statistically significant improvement over all control treatments.

| Rating Scale |
|---|
| 1) non-symptomatic |
| 2) localized necrosis |
| 3) round sporulating lesion |
| 4) vertical lesion spread |
| 5) Horizontal lesion spread |
| 6) coalesced lesions |
| 7) Cleistothecia visible in mycelium |

These data show a statistically significant ($\alpha=0.05$) decrease in the disease severity observed in wheat heads among the 5 ppm and 25 ppm glycolic acid treated wheat versus the control wheat, and in wheat leaves among all glycolic acid treated wheat versus control wheat.

EXAMPLE 4

Effect of Glycolic Acid on the Resistance and/or Tolerance of Lettuce to the Effects of Post-Harvest-Induced Pathogen Stress Waldmann's MTO dark green Grand Rapids leaf lettuce seed, lot# 15529, was purchased from Johnny's Selected Seeds, Albion, Me., and grown 8 plants per 1 gallon pot. Circular steel-blue blotter papers (Anchor Paper Co, St. Paul, Minn.) were steam autoclaved and fitted into disposable petri dishes. Treatments consisted of non-inoculated and inoculated groups of non-treated (NTC), water and 0.01% surfactant-blank (SB) controls and 10, 25, 75, 500 and 1000 ppm of glycolic acid.

Blotters were saturated with 4.5 ml sterile tap water. Individual leaves (20) were excised and placed into a treatment solution for 5–10 seconds or left non-treated. Excess fluid was removed from the leaf surface. These leaves were then placed singly, 1 leaf per dish and adaxial side up, on the moist blotters. Dish lids were replaced and dishes stacked, bagged and returned to the petri dish box for 24 hour dark storage at room temperature (65–68° F.).

Inoculum (*Bottytis cinerea*) was grown on potato dextrose agar (PDA) plates until dense conidia production was present. These were blended into a paste with non-inoculated PDA and sterile tap water. Inoculum concentration was determined by dilution plating to be 1960 cfu/ml.

A small spot of inoculum paste was dotted onto the center of 16 of the 20 leaf pieces per treatment stack 24 hours after test substance application.

Disease progression assessment was made at 3 days±2 hours post-inoculation by measuring the radius of colonized tissue in mm. The results are shown below in Table 4.

TABLE 4

| Treatment | Average Disease Progression (mm) |
|---|---|
| NTC | 11.3 |
| Water | 8.4 |
| SB | 11.8 |
| 10 ppm | 4.0* |
| 25 ppm | 9.8 |
| 75 ppm | 9.4 |
| 150 ppm | 13.6 |
| 500 ppm | 12.1 |
| 1000 ppm | 11.6 |

*indicates a statistically significant improvement over all control treatments.

These data show a statistically significant ($\alpha=0.05$) decrease in the disease severity with the 10 ppm glycolic acid treated lettuce leaves versus the control lettuce.

EXAMPLE 5

Effect of Glycolic Acid on the Resistance and/or Tolerance of Lettuce to the Effects of Post-Harvest-Induced Pathogen Stress Waldmann's MTO dark green Grand Rapids leaf lettuce seed, lot# 15529, was purchased from Johnny's Selected Seeds, Albion, Me., and broadcast seeded into 10×20×2' flats. Circular steel-blue blotter papers (Anchor Paper Co, St. Paul, Minn.) were fitted into disposable petri dishes. Treatments consisted of non-inoculated and inoculated groups of non-treated (NTC), water and 0.01% surfactant-blank (SB) controls and 10, 25, 75,150, 500 and 1000 ppm of glycolic acid.

Blotters were saturated with 4.5 ml sterile tap water. Individual leaves (20) were excised and placed into a treatment solution for 5 seconds or left non-treated. Excess fluid was removed from the leaf surface. These leaves were then placed singly, 1 leaf per dish and adaxial side up, on the moist blotters. Dish lids were replaced and dishes stacked, bagged and returned to the petri dish box for 24 hours dark storage at room temperature (68–72° F.).

Inoculum (*Sclerotinia minor* hyphal fragments and sclerotia) was grown on potato dextrose agar (PDA) plates until the sclerotia were black and hard. These were blended into a paste with non-inoculated PDA and sterile tap water. A small spot of inoculum paste containing hyphal fragments and 2–3 sclerotia was dotted onto the center of 16 of the 20 leaf pieces per treatment stack 24 hours after test substance application.

Due to the nature of Sclerotinia as a pathogen, disease is generally an all-or-nothing phenomenon. Therefore, it is necessary to assess both disease incidence and disease severity to give an accurate representation of the disease progression. Disease severity assessment was made at 3 days±2 hours post-inoculation by measuring the radius of colonized tissue in mm. Disease incidence was assessed as the presence or absence of infection (number of diseased leaves/ number of leaves tested) 100=% incidence. Multiplying the average severity by the % incidence and dividing by 100 then combined both evaluations into one assessment number and created a disease index value. The results in Table 5 below show this value for each treatment.

TABLE 5

| Treatment | Disease Index [(severity)(% incidence)/100] |
|---|---|
| NTC | 4.1 |
| Water | 2.0 |
| SB | 23.6 |
| 10 ppm | 1.2 |
| 25 ppm | 0.1* |
| 75 ppm | 0.5* |
| 150 ppm | 1.3 |
| 500 ppm | 1.1 |
| 1000 ppm | 2.0 |

*indicates a statistically significant improvement over all control treatments.

These data show a statistically significant ($\alpha=0.05$) decrease in the disease severity with the 25 ppm and 75 ppm glycolic acid treated lettuce leaves versus the control lettuce.

EXAMPLE 6

Effect of Glycolic Acid on the Resistance and/or Tolerance of Cabbage Plants to the Effects of Cold and Drought Stress Seeds of Heads Up cabbage were obtained from Harris Seeds, Rochester, N.Y. and grown in 7"×5¼"×2¼" (17.78 cm×13.34×5.72 cm) Kord inserts (Park Seeds, Greenwood, S.C.) containing Bacto potting soil (Michigan Peat Company, Houston, Tex.). After plants had germinated, cabbage seedlings were thinned to six plants per insert. Inserts were kept in 12"×8¾" (30.48 cm×22.23 cm) perma nest trays (Park Seed) with two inserts per tray. Each treatment consisted of three replicate trays containing a total of eighteen cabbage plants. After 12 days, some of the plant were sprayed with Glypure® at 25 ppm, 100 ppm, and 200 ppm. Treated plants were given a second application of Glypure® 7 days later. Untreated and treated plants were subjected to freeze and heat shock treatments 24 hours later. Cold shock was administered by exposing plants to −3° C. for 2 hours and 20 minutes. Heat treatment was provided by placing plants in an oven for 5 hours at 46.5° C. One week following the temperature treatments, the plants were harvested and the fresh and dry weights were determined. Results are shown in Table 6 below.

TABLE 6

| Treatment | Avg. Fresh Weights ± SD† | Avg. Dry Weights ± SD† |
|---|---|---|
| Room Temp. Control | 28.6 ± 5.4 | 5.8 ± 0.3 |
| Cold Stress Control | 22.6 ± 9.2 | 2.3 ± 0.7 |
| Cold Stress + Glypure ® 25 ppm | 28.6 ± 2.7 | 3.1 ± 0.1 |
| Cold Stress + Glypure ® 200 ppm | 31.4 ± 1.3 | 3.2 ± 0.2 |
| Heat Stress Control | 11.6 ± 1.1 | 2.6 ± 0.05 |
| Heat Stress + Glypure ® 25 ppm | 10.2 ± 2.6 | 2.5 ± 0.3 |
| Heat Stress + Glypure ® 200 ppm | 15.2 ± 0.6 | 3.5 ± 0.1 |

†standard deviation

The results in Table 6 demonstrate that treating plants with glycolic acid prior to temperature stress enabled plants to better tolerate the growth-limiting effects of the adverse temperatures. The reduction in fresh and dry weights, caused by the adverse temperatures, was statistically significantly lower in plants treated with glycolic acid at 200 ppm than in untreated plants.

EXAMPLE 7

Effect of an Ammonium Salt of Glycolic Acid on Stimulating Plant Growth

Market Prize, F1 cabbage seed, lot 88955, was purchased from Harris Seeds, Inc. (Rochester, N.Y.) and grown 2 plants per 4"×4"×4" pot, 1 pot per experimental unit and 6 experimental units per each of 4 replications. The plants were spray-treated first at 2 true leaves and again 7 days later with 8 ml solution per pot.

Figure 1:
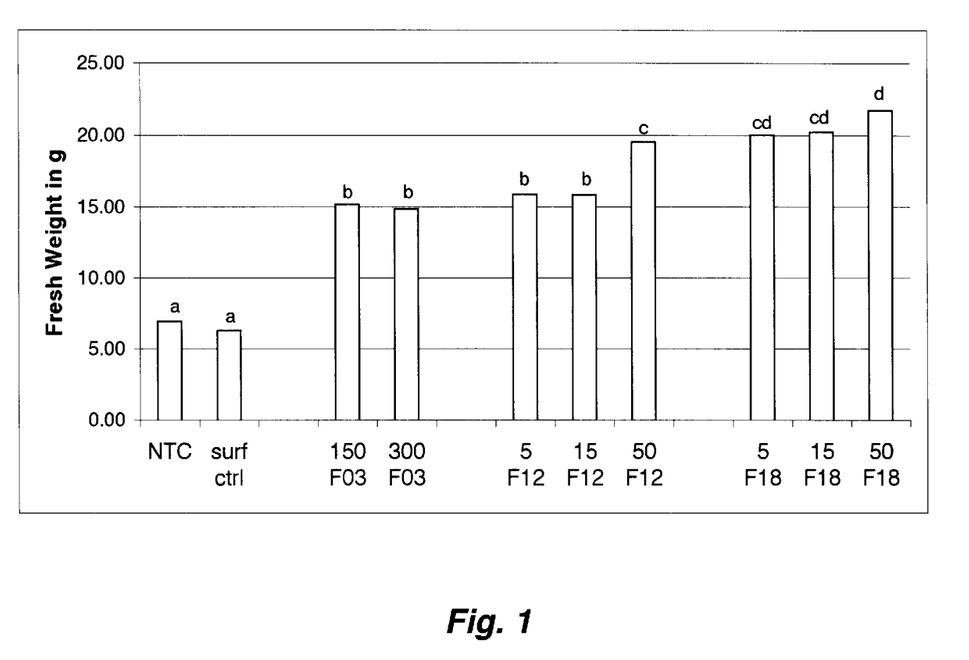
FIG. 1 is a graph showing the fresh weight of cabbage after being treated with the indicated concentrations (in ppm, on a weight/volume basis) of Auxigro (F03, a 1:1:1 solution of γ-aminobutyric acid, glutamic acid and casein hydrolysate), glycolic acid (F12) or ammonia-neutralized glycolic acid (F18) as described in example 7. NTC, non-treated control; surf ctrl, surfactant control (surfactant is Breakthru®, a silicone-based surfactant); a, b, c, cd, and d represent Duncan groupings.
Figure 2:
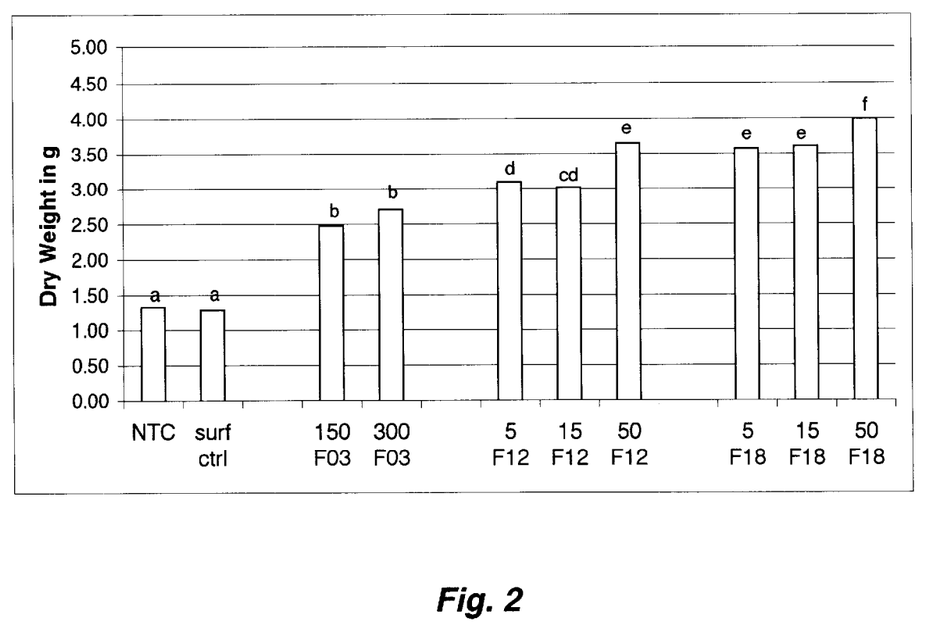
FIG. 2 is a graph showing the dry weight of the cabbage treated with either F03, F12 or F18 as in FIG. 1. NTC, non-treated control; surf ctrl, surfactant control (surfactant is Breakthru®, a silicone-based surfactant); a, b, d, cd, e, and f represent Duncan groupings.

The treatments included a non-treated control (NTC), 0.05% Breakthru® (a silicone-based surfactant obtained from Goldschmidt Chemical, Hopewell, Va.) control, and 5, 15 or 50 ppm of either Glypure® (F12; 99% high purity crystalline glycolic acid), or ammonia-neutralized Glypure® [F18; a 50% (w/v) solution made by neutralizing 70% high purity glycolic acid from DuPont with ammonium hydroxide to a pH of 4.4. The results are shown in FIGS. 1 and 2. Growth stimulation was assessed by measuring both the fresh and dry weights of the plants.

As seen in FIGS. 1 and 2, application of F18 to plants statistically significantly stimulated plant growth compared to the controls. It is also seen in FIGS. 1 and 2 that F18 surprisingly stimulated plant growth to a greater extent than the plants treated with equivalent amounts of F12 (e.g., plants treated with 5 ppm F18 exhibited a statistically significantly greater stimulation of plant growth compared to plants treated with 5 ppm F12, etc.).

EXAMPLE 8

Effect of Glycolic Acid and Ammonium Glycolate on Increasing the Resistance of Plants to the Effects of Drought Stress Market Prize, F1 cabbage seed, lot 88955, as described in example 7, was treated identically as in example 7, except that drought stress was imposed by withholding water 7 days following the second spray and continuing to withhold water for 13 sequential days thereafter. Drought tolerance was assessed by measuring both the fresh and dried weights of the plants. The results are shown in FIGS. 3 and 4.

Figure 3:
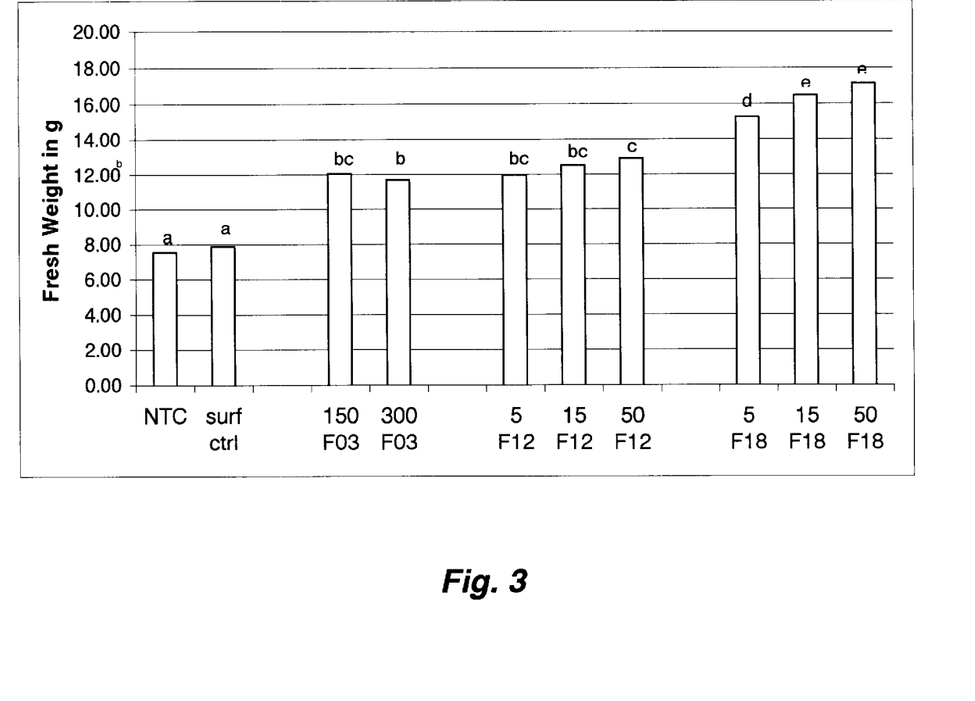
FIG. 3 is a graph showing the fresh weight of cabbage after being treated with the indicated concentrations (in ppm, on a weight/volume basis) of F03, F12 or F18 and exposed to drought conditions as described in example 8. NTC, non-treated control; surf ctrl, surfactant control (surfactant is Breakthru®, a silicone-based surfactant); a, bc, b, c, d, and e represent Duncan groupings.
Figure 4:
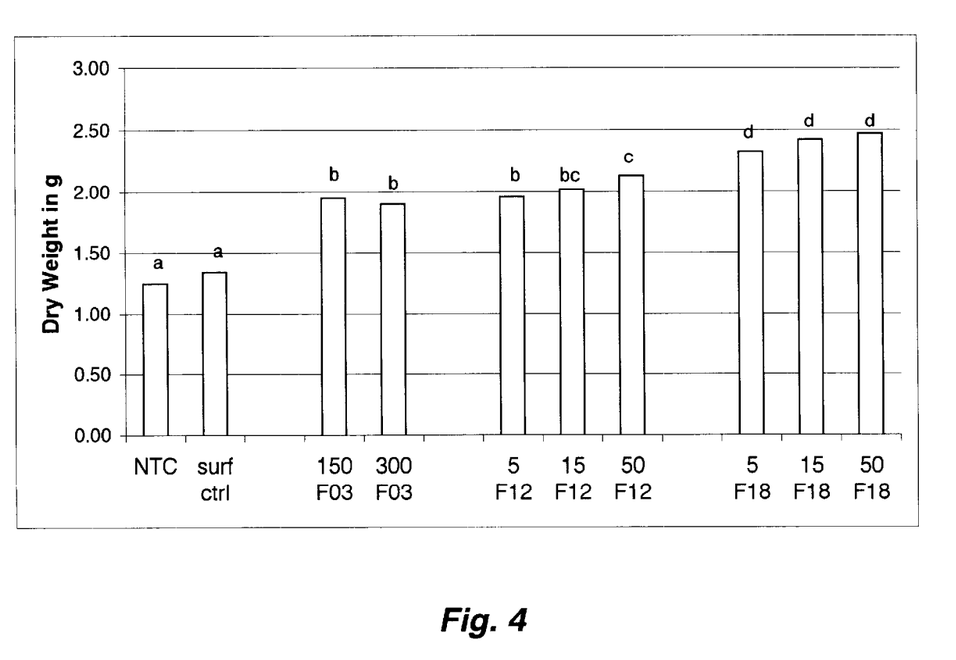
FIG. 4 is a graph showing the dry weight of cabbage treated with F03, F12 or F18 as in FIG. 3. NTC, non-treated control; surf ctrl, surfactant control (surfactant is Breakthru®, a silicone-based surfactant); a, b, bc, c and d represent Duncan groupings.

As seen in FIGS. 3 and 4, application of either F12 or F18 to the cabbage statistically significantly increased the fresh weight (FIG. 3) and the dry weight (FIG. 4) of the cabbage compared to controls. Moreover, application of F18 surprisingly had a statistically significantly greater effect on increasing the resistance of the cabbage to the effects of drought stress than the plants treated with equivalent amounts of F12. That is, plants treated with 5, 15 and 50 ppm of F18 weighed statistically significantly more than the plants treated with 5, 15 and 50 ppm F12, respectively.

EXAMPLE 9

Effect of Glycolic Acid on the Resistance and/or Tolerance of Plants to the Effects of Plant Stress Glycolic acid, and salts thereof, can be used to increase the resistance of a plant to the effects of plant stress. Plants can be treated as described in Examples 1–5 above with glycolic acid. The plants can be treated with glycolic acid in amounts of about 1 ppm to about 10,000 ppm [about 0.013 oz/acre (oz/A) to about 8.3 lbs/A] [about 0.93 g/hectare (g/ha) to about 9.4 kg/ha]. However, the plants are more preferably treated with glycolic acid in amounts of about 1 ppm to about 5,000 ppm [about 0.013 oz/A to about 4.2 lbs/A] [about 0.93 g/ha to about 4.7 kg/ha], about 1 ppm to about 1000 ppm [about 0.013 oz/A to about 0.83 lbs/A] [about 0.93 g/ha to about 0.94 kg/ha] and about 2 ppm to about 500 ppm [about 0.027 oz/A to about 0.42 lbs/A] [about 1.9 g/ha to about 0.47 kg/ha]. Glycolic acid, salts thereof, and mixtures thereof, are useful in increasing the resistance and/or tolerance of the plants to the various forms of stress described in Examples 1–6 and 8 above, including mechanical damage stress, nutrient stress, heat stress, cold stress, drought stress, water stress, and pathogen stress (including insect, bacterial, fungal and viral pathogen stresses).

EXAMPLE 10

Effect of Glycolic Acid-Containing Compositions on the Growth of a Plant Pathogen

*Sclerotinia minor* culture SaM-18 was received from Krishna Subbarro, Ph.D., Univ. Calif., Davis. Potato dextrose agar (PDA) powder was purchased from Baltimore Biological Laboratory, Inc. (BBL), ammonium glycolate and glycolic acid from DuPont Specialty Chemicals and BreakThru® surfactant from Goldschmidt Chemical Corp.

PDA was made, poured into sterile disposable petri dishes (100×15 mm) and inoculated with *S. minor* sclerotia to start new cultures on day zero. These cultures had reached an appropriate stage of maturation for use for use in the test after two weeks of growth. Multiple 1 liter containers of PDA were made and autoclaved on day 14. These PDA containers remained in the circulating water bath at 46° C. until the solutions were ready for addition (about 2 hrs.). The glycolic acid-containing compositions were added to the 46° C. PDA through a syringe-tip 0.2 $\mu$m-pore sterile filtration disc in a positive laminar-flow sterile hood and thoroughly mixed before returning to the 46° C. water bath to await pouring. Stacks of 22 dishes were poured for each medium type and allowed to solidify and cool overnight.

On day 15, soft, white to gray, sclerotial clumps of hyphae were picked from the culture dishes with heat sterilized forceps and one clump was transferred to the center of each test medium dish. Twenty dishes of each inoculated medium were stacked and replaced into the plastic sleeves they were originally packaged in for incubation at room temperature (about 23° C.). After 4 days of growth, some of the cultures had just reached the edges of the medium. The radius of each colony was measure in mm.

Treatments were water controls, 0.05% surfactant controls, 5, 15, 50, 75 and 100 ppm of glycolic acid (F12) and 5, 15, 50, 100 and 750 ppm of ammonia-neutralized glycolic acid (F18; i.e., ammonium glycolate).

Figure 5:
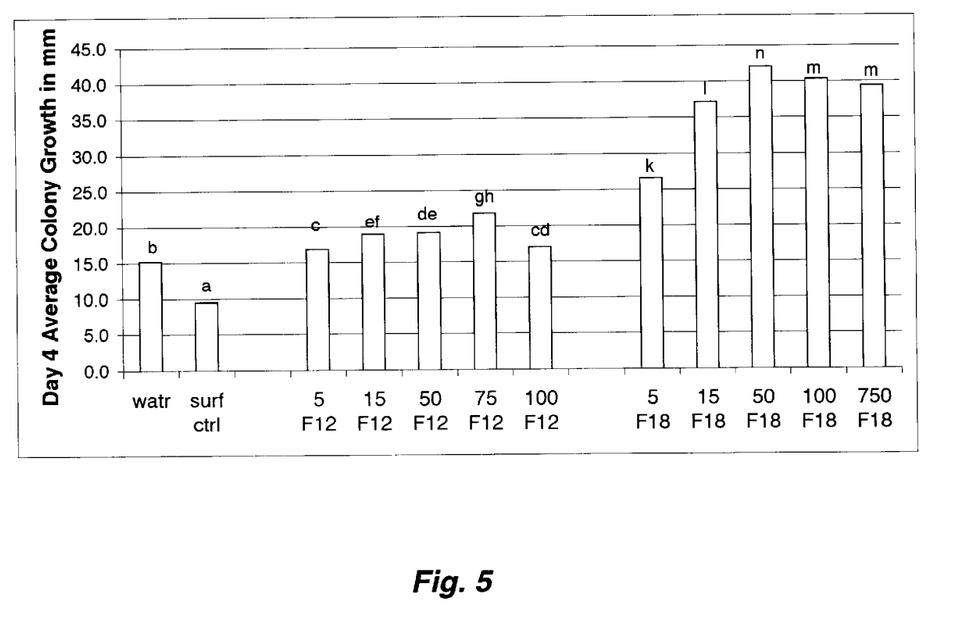
FIG. 5 is a graph showing the average radius of *Sclerotinia minor* colonies after treatment with the indicated concentrations of F12 and F18 as described in example 10. watr, water control; a, b, c, cd, de, ef, gh, k, I, m, and n represent Duncan groupings.

As can be seen in FIG. 5, treatments with F12 and F18 surprisingly statistically significantly increased the growth of *Sclerotinia minor* compared to controls. The data in FIG. 5 also demonstrates that ammonium glycolate increased Sclerotinia growth significantly more than equivalent amounts of glycolic acid.

While the invention has been illustrated and described in detail in the examples and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method of increasing the resistance of a plant to the effects of plant stress, comprising treating the plant with an amount of an ammonium glycolate salt, effective in increasing the resistance of the plant to the effects of plant stress.

2. The method of claim 1, wherein said treating is with a composition that includes at least one additional active agent.

3. The method of claim 2, wherein said active agent is selected from the group consisting of fertilizers, herbicides and pesticides.

4. A method of increasing the resistance of a plant to the effects of plant stress, comprising:

(a) predicting when a stressful condition will arrive; and (b) treating the plant with glycolic acid, a salt thereof, or a mixture thereof prior to the occurrence of plant stress.

5. The method of claim 4, wherein said glycolic acid is combined with a carrier medium.

6. The method of claim 5, wherein said carrier medium is aqueous or solid.

7. The method of claim 4, wherein the plant is treated with an amount of glycolic acid, a salt thereof, or a mixture thereof, effective in increasing the resistance of the plant to the effects of plant stress.

8. The method of claim 7, wherein the plant is treated with about 0.5 ppm to about 5,000 ppm of glycolic acid on a weight volume basis.

9. The method of claim 8, wherein the plant is treated with about 1 ppm to about 1000 ppm of glycolic acid on a weight/volume basis.

10. The method of claim 4, wherein said stress is selected from the group consisting of pathogen stress, heat stress, cold stress, salt stress, mechanical damage stress, drought stress, and water stress.

11. A method of increasing the resistance of a plant to the effects of plant stress, comprising treating the plant with glycolic acid, a salt thereof, or a mixture thereof prior to the occurrence of plant stress.

12. The method of claim 11, wherein said plant is treated with an amount of glycolic acid, a salt thereof, or a mixture thereof, effective in increasing the resistance of the plant to plant stress.

13. The method of claim 11, wherein the plant is treated with about 0.5 ppm to about 5,000 ppm of glycolic acid on a weight/volume basis.

14. The method of claim 13, wherein the plant is treated with about 1 ppm to about 1000 ppm of glycolic acid on a weight/volume basis.

15. The method of claim 14, wherein the plant is treated with said glycolic acid at a rate of about 0.013 oz/A to about 0.83 lbs/A.

16. The method of claim 11, wherein said stress is selected from the group consisting of pathogen stress, heat stress, cold stress, salt stress mechanical damage stress, drought stress, and water stress.

17. The method of claim 11, wherein said treating is with a composition that includes at least one additional active agent.

18. The method of claim 17, wherein said active agent is selected from the group consisting of fertilizers, herbicides, pesticides and combinations thereof.

19. A method of treating a plant, comprising treating the plant with about 1 ppm to about 5000 ppm of ammonium glycolate to stimulate plant growth.

20. The method of claim 19, wherein said ammonium glycolate is combined with a carrier medium.

21. The method of claim 20, wherein said carrier medium is aqueous or solid.

22. The method of claim 19, wherein said treating is with a composition that includes at least one additional active agent.

23. The method of claim 22, wherein said additional active agent is selected from the group consisting of fertilizers, herbicides, pesticides and combinations thereof.

24. The method of claim 19, wherein the plant is treated with about 1 ppm to about 1000 ppm of ammonium glycolate.

25. A method of treating a plant, consisting essentially of treating said plant with an amount of ammonium glycolate effective in stimulating plant growth.

26. A method of increasing microbial growth, comprising treating the microbe with an effective amount of ammmonium glycolate.

27. The method of claim 26, wherein said microbe is treated with about 1 ppm to about 500 ppm of ammonium glycolate on a weight/volume basis.

* * * * *